United States Patent [19]

Bullock

[11] Patent Number: 4,967,031

[45] Date of Patent: Oct. 30, 1990

[54] HYDROGENATION USING HYDRIDES AND ACID

[75] Inventor: R. Morris Bullock, Wading River, N.Y.

[73] Assignee: The United States of America as represented by the United States Department of Energy, Washington, D.C.

[21] Appl. No.: 449,181

[22] Filed: Dec. 13, 1989

[51] Int. Cl.$^5$ ............................................... C07C 5/00
[52] U.S. Cl. .................................. 585/250; 585/275; 585/277; 585/469; 585/639; 585/733
[58] Field of Search ............... 585/250, 275, 277, 469, 585/639, 733

[56] References Cited

U.S. PATENT DOCUMENTS 4,133,840  1/1979  Inamoto et al. ..................... 585/275

*Primary Examiner*—Curtis R. Davis
*Attorney, Agent, or Firm*—Margaret C. Bogosian; James W. Weinberger; William R. Moser

[57] ABSTRACT

A process for the non-catalytic hydrogenation of organic compounds, which contain at least one reducible functional group, which comprises reacting the organic compound, a hydride complex, preferably a transition metal hydride complex or an organosilane, and a strong acid in a liquid phase.

19 Claims, No Drawings

HYDROGENATION USING HYDRIDES AND ACID

This invention was made with Government support under contract number DE-AC No. 02-76CH00016, between the U.S. Department of Energy and Associated Universities, Inc. The Government has certain rights in the invention.

BACKGROUND OF THE INVENTION

The present invention relates to a very rapid, non-catalytic process for hydrogenating unsaturated organic compounds that can be carried out at temperatures generally lower than previously utilized.

Hydrogenation reactions involve the addition of hydrogen whereby, for example, an alkene can be reduced to an alkane. The smaller alkanes can be obtained directly from petroleum or natural gas. Above pentane, however, alkanes must be synthesized, generally by hydrogenating alkenes. Prior art processes have generally required the presence of a catalyst along with relatively high hydrogen pressure and elevated temperature. Catalysts used in such hydrogenation of alkenes are usually heterogeneous with a solid phase of e.g. platinum, palladium or nickel. Similar catalytic processes have been used to hydrogenate unsaturated alcohols to saturated alcohols, and unsaturated esters to saturated esters.

Catalyzed hydrogenations of unsaturated organic compounds also have been carried out using transition metal hydrides as catalysts. U.S. Pat. No. 3,644,445 to Kroll, et al. discloses a transition metal carbonyl hydride complexed with an organo-metallic compound to form a catalyst for hydrogenation. A transition metal complex such as Wilkinson's catalyst $Rh[(C_6H_5)_3P]_3Cl$, has been used in homogeneous processes to hydrogenate unsaturated compounds containing isolated olefinic and acetylenic linkages [Osborn, J. A., et al., *J. Chem. Soc. (A)*, 1711–1732 (1966)].

U.S. Pat. No. 3,883,607 to Neikam describes the use of a heated transition metal hydrate, $H_2MoO_3$ as a source of hydrogen in the hydrogenation of an olefin at elevated temperature. U.S. Pat. No. 2,856,428 to Brown discloses a method for reducing functional groups of organic compounds using alkali metal borohydride and aluminum chloride to react with the organic compound at 25° C.

Non-catalytic ionic hydrogenation using organosilanes and trifluoroacetic acid has been disclosed by Kursanov, D. N., et al., *Synthesis* 1974, 633–651 (1974). The Kursanov, et al. method for the hydrogenation of alkenes requires a temperature of 50° C., a time of at least several hours, and prohibits the use of strong acids.

The reduction of aryl and diaryl ketones to hydrocarbons by the slow addition of trifluoromethanesulfonic acid to the ketone in dichloromethane solution, followed by the addition of triethylsilane and stirring at room temperature for a few hours, is disclosed by Olah, G, et al., *Synthesis* 1986, 770–772 (1987).

It is an object of the present invention to provide a non-catalytic process for the hydrogenation of organic compounds quickly and efficiently. It is a further object to provide a non-catalytic method for hydrogenating highly substituted alkenes, secondary benzylic alcohols, tertiary alcohols and compounds containing strained cyclic groups. It is another object to provide a very rapid method for the hydrogenation of alkenes at low temperatures with very high product yield. It is yet another object to facilitate hydrogenation of organic compounds by metal hydrides or silanes with the addition of a strong acid to the reaction medium.

SUMMARY OF THE INVENTION

The present invention relates to a process whereby organic compounds which contain at least one reducible functional group are hydrogenated non-catalytically by reacting them with a hydride complex and a strong acid. The reducible functional group may be, for example, C=C, C—OH, C—O—C, or a strained cyclic structure. If the reactants are not mutually soluble, they are dissolved in an appropriate inert solvent.

The present invention further relates to a process for the non-catalytic hydrogenation of aromatic ketones by reacting said ketones with a transition metal hydride complex selected from the group consisting of $HMo(CO)_3(C_5H_5)$, $HMn(CO)_5$, $HW(CO)_3(C_5H_5)$, $HFe(CO)_2(C_5H_5)$, $HMn(PF_3)_5$, $HRe(CO)_5$, $HCo(CO)_4$ and $HCo(PF_3)_4$, and a strong acid in a liquid phase.

In one aspect of the present invention, the rapid, non-catalytic hydrogenation of a substituted alkene is accomplished by adding a strong acid to a liquid phase containing the alkene and a hydride complex selected from the group consisting of $HMo(CO)_3(C_5H_5)$, $HW(CO)_3(C_5H_5)$, $HMn(CO)_5$ and organosilanes.

The present invention permits the hydrogenation of a variety of organic compounds at low temperature and pressure and with very high product yields.

For a better understanding of the present invention, together with other and further objects, reference is made to the following description, and its scope will be pointed out in the appended claims.

DETAILED DESCRIPTION OF THE INVENTION

The process described herein can be used for a variety of hydrogenation reactions. As used herein, hydrogenation means the reaction of hydrogen with an organic compound, and encompasses processes that can also be called reduction whereby electrons are accepted by a compound, hydrogen is added to a compound, or oxygen is removed from a compound while hydrogen is added.

Using the process of this invention, unsaturated organic compounds can be hydrogenated to give the corresponding saturated derivatives. Unsaturated carbon-carbon bonds can be saturated; the C-OH groups of alcohols and the C—O—C portion of esters can be reduced; and ring openings of strained cyclic groups can be accomplished. Organic compounds which may be hydrogenated in accordance with the present invention include but are not limited to alkenes, tertiary alcohols, secondary benzyl alcohols, and compounds containing strained cyclic groups such as cyclopropyl. In these hydrogenations, internal olefinic bonds are hydrogenated in preference to terminal olefinic bonds and oxygen can be removed from alcohols. Feeds containing carbon-carbon unsaturation may be acetylenic, olefinic, cyclic, aromatic, or mixtures thereof and may contain dienes and trienes. The hydrogenation of alkenes involves the overall addition of two hydrogen atoms to the carbon-carbon double bond to result in the formation of the corresponding alkane. It is known that tri- and tetra- substituted alkenes are difficult to hydrogenate because of their greater stearic bulk. The process of the present invention specifically addresses this difficulty.

Alkenes which can be hydrogenated using the process of the present invention include cycloalkenes, arylalkenes, alkenylcyclopropenes and their derivatives. The instant process is very advantageous when used to hydrogenate hindered alkenes which are tetra-substituted, trisubstituted, and 1,1-disubstituted. Highly substituted alkenes are preferred as substrates and the instant process is most effective for unsaturated carbon-carbon compounds which have at least four carbons, are substituted, have ethylenic unsaturation, and they are capable of forming carbonium ions. Typical examples of the alkenes useful herein are substituted butenes, pentenes, cyclopentenes and the like.

The substituted alkenes that can be hydrogenated using the process of the present invention may be represented by the formula

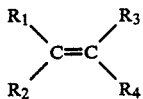

wherein $R_1$, $R_2$, $R_3$ and $R_4$ are selected from the group consisting of aliphatic or olefinic groups having from 1 to 20 carbon atoms, —C≡N, —NO$_2$, esters (—OCO—), ethers (COC), carbonyls, halides, ketones, thiol, aldehydes, —H, —COOR, aryl, and aryl halide. Regardless of the functional group chosen for $R_1$–$R_4$, the internal olefinic bond of a hindered alkene is preferentially hydrogenated.

Alcohols which can be hydrogenated include tertiary alcohols and secondary benzyl alcohols. Examples of aromatic alcohols which can be treated are di-methylbenzyl alcohol and α-methylbenzyl alcohol. Ring opening of compounds containing a cyclopropyl group may be accomplished. The hydrogenation of aromatic ketones may be accomplished using transition metal hydrides.

The hydrides that are useful in the practice of the present invention include transition metal hydrides and silane complexes. The hydride employed for the hydrogenation must be stable to the unsaturated organic compound being treated. As used herein, hydride complexes are defined as complexes containing a hydride ligand bonded to a central atom, the central atom also being bonded to one or more ligands.

The transition metal hydrides that may be used in the present invention generally have the form H-M-L wherein H is hydrogen, M is a transition metal selected from Groups VB through VIII of the Periodic Table (new Periodic Table notation Groups 6 through 10), such as molybdenum, tungsten, manganese, rhenium, iron, and cobalt, and L is a ligand. Ligands may be, for example, carbonyl (CO), cyano (CN), triphenylphosphine [P(C$_6$H$_5$)$_3$], cyclopentadienyl (C$_5$H$_5$) and trifluorophosphine (PF$_3$). Preferred transition metals are molybdenum, tungsten and manganese. Preferred ligands are carbonyl and cyclopentadienyl. Generally, early transition metals to the left in the Periodic Table such as zirconium are not suitable as M herein because they will undergo undesirable reaction with the acid. Preferably the transition metal is in the form of a hydridocarbonyl, hydridocyclycopentadienyl, a hydridocarbonylcyclopentadienyl, or a hydridotrifluorophosphine, for example [HMo(CO)$_3$(C$_5$H$_5$)] [HW(CO)$_3$(C$_5$H$_5$)], [HMn(CO)$_5$] or [HFe(CO)$_2$(C$_5$H$_5$)]. Other hydrides which may be used are [HMn(PF$_3$)$_5$], [HRe(CO)$_5$], [HCo(CO)$_4$], and [HCo(PF$_3$)$_4$].

Preferred hydrides in the process of the invention are HMo(CO)$_3$(C$_5$H$_5$), HW(CO)$_3$(C$_5$H$_5$), HMn(CO)$_5$, and HSi(CH$_2$CH$_3$)$_3$.

Silane complexes useful in the present process are organosilanes such as di- and trialkylsilanes. Useful silanes in the process of the present invention include triethylsilane, HSi(CH$_2$CH$_3$)$_3$, diethylsilane, H$_2$Si(CH$_2$CH$_3$)$_2$, diphenylsilane, H$_2$Si(C$_6$H$_5$)$_2$, and tri-n-propyl silane, HSi(CH$_2$CH$_2$CH$_3$)$_3$.

The process of the invention is non-catalytic so that the hydride complex exhibits true hydridic behavior, acting as a hydride donor and entering into the stoichiometry of the reaction. Therefore, the hydride complex is depleted as the unsaturated organic compound is hydrogenated. The hydrides are prepared by conventional methods.

In addition to the hydride complexes described above, a strong acid is also used in the process of the invention. For purposes of this invention, the term strong acid refers to acids with a pK$_a$ less than about 1. Acids with a pK$_a$ less than about −0.5 are preferred. The counterions or conjugate bases of these acids must also have low coordinating ability so that the counterion does not coordinate with an intermediate compound in the process of the invention.

Bronsted acids are the preferred acids. Representative acids which may be employed include, for example, organic sulfonic acids such as trifluoromethanesulfonic acid (CF$_3$SO$_3$H), fluorosulfonic acid (FSO$_3$H), toluene sulfonic acid (CH$_3$)C$_6$H$_4$(SO$_3$H) and methane sulfonic acid (CH$_3$SO$_3$H); tetrafluoroboric acid-ether complexes such as HBF$_4$.OEt$_2$; hexafluorophosphoric acid-ether complexes such as HPF$_6$.OEt$_2$; and sulfuric acid. Preferred acids are CF$_3$SO$_3$H, FSO$_3$H, and HBF$_4$.O(C$_2$H$_5$)$_2$.

The reactions herein will be run in a liquid phase, that is, reaction components are dissolved in an organic solvent. Any solvent which is chemically inert and which does not interfere with the hydrogenation reaction may be employed. The solvents may be paraffinic, preferably having 5 through 20 carbons such as pentane, heptane, octane, etc.; C$_6$ through C$_{12}$ aromatics such as toluene, xylene, mesitylene and benzene; or halogenated aromatics. Preferred solvents are dichloromethane (methylene chloride) and toluene. If the reactants are mutually soluble, the use of a solvent is not necessary. In addition, the substrate and acid need be only partially soluble or may be completely soluble in the solvent.

In the hydrogenation process of the invention, a high yield of hydrogenated product is obtained with a great flexibility in temperatures used. The process may be carried out from about −110° C. to about 111° C. and a limiting factor is the freezing or boiling point of the solvent and reactants. A preferred temperature range is from about −95° C. to about 60° C., with from about 0° to about 25° C. most preferred for the sake of convenience. At room temperature, hydrogenation of alkenes to alkanes can take place very rapidly, indeed in a matter of seconds. At temperatures as low as −80° C., the reaction is completed in minutes.

When hydrogenating alkenes, to avoid reactions between the organic substrate and the acid which may cause unwanted polymerization, the unsaturated organic compound and the hydride complex are first dissolved in the solvent, then the acid is added.

The unsaturated organic compound, hydride complex and acid may be used in stoichiometric amounts with respect to each other. The ratio of substrate to hydride present in the reaction may be from about 99:1 to 1:99 with a 50:50 molar ratio of substrate to hydride preferred and an excess of hydride from about 20% to about 30% over substrate being most preferred. The ratio of substrate to acid present in the reaction may be from about 99:1 to 1:99 with a 50:50 molar ratio of substrate to acid preferred and an excess of acid from about 20% to about 30% over substrate being most preferred. The reaction is preferably carried out in an inert atmosphere and in the absence of oxygen.

When the process is used to hydrogenate alkenes, the reaction is very rapid and is complete at room temperature within the time of mixing; i.e., instantaneously or within seconds. At −78° C., the reaction is complete within minutes. When tertiary alcohols or secondary benzylic alcohols are hydrogenated, the reaction is complete within about 5 hours at room temperature. Hydrogenation of aromatic ketones requires a few minutes using $CF_3SO_3H/HMo(CO)_3(C_5H_5)$ but requires several hours for $CF_3SO_3H/HW(CO)_3(C_5H_5)$. Ring opening of cyclic compounds containing cyclopropyl groups is complete within about an hour.

The process may be carried out at ambient pressure and in any type of apparatus which enables intimate contact of the reactants and control of operating conditions. The hydrogenated product may be removed by known means such as distillation and chromatography.

The invention can be illustrated by the following examples:

EXAMPLE 1

In an inert atmosphere drybox at room temperature, 2,3-dimethyl-2-butene (5 microliters, 0.042 millimoles) and metal hydride $(C_5H_5)(CO)_3MoH$ (19 mg, 1.8 equivalents based on starting alkene), along with an $^1H$ Nuclear Magnetic Resonance (NMR) internal standard of 2 microliters of mesitylene were added to a 5 mm NMR tube. Benzene-$d_6$ solvent was added to give a total volume of 0.45 ml. Trifluromethane-sulfonic acid ($CF_3SO_3H$, 7 microliters, 1.9 equivalents based on starting alkene) was added. The tube was shaken. An immediate color change from yellow to dark wine-red indicated very rapid hydrogenation. After five minutes an $^1H$ NMR spectrum indicated a 91% yield of 2,3-dimethylbutane.

EXAMPLES 2-8

Using the method of Example 1, other alkenes were hydrogenated. Details of the type and amount of reagents, the solvents and the resulting products are listed in Table I. The reactions were as rapid as that of Example 1.

COMPARATIVE EXAMPLES

When the strong acid is added first to a solution of an organic compound to be hydrogenated at either room temperature or low temperatures of −75° C., before transition metal hydride or silane are added, the organic compound polymerizes and hydrogenation cannot be carried out.

Experiments were carried out to show that unwanted side reactions occur when there is no hydride or silane present before the acid is added to the organic compound.

A. In one experiment, 2,3-dimethyl-2-butene (7 microliters) was mixed with $CF_3SO_3H$ (10 microliters) in benzene-$d_6$ (ca. 0.4 mL). The solution became cloudy immediately upon addition of the acid. After 30 minutes in $^1H$ NMR spectrum indicated that all of the alkene had been consumed. New resonances in the NMR spectrum were observed that are presumably due to polymerized product.

B. Another experiment was carried out under similar conditions using 2-ethyl-1-butene and $CF_3SO_3H$. Analogous results were obtained, with none of the alkene observed by NMR spectroscopy after 30 minutes at room temperature.

EXAMPLES 9-14

TABLE I

Alkene Hydrogenations at Room Temperature (ca. 22° C.) using $CF_3CO_3H$ and $(C_5H_5)(CO)_3MH$ (M = Mo,W)

| Example | Alkene (Millimoles) | $CF_3SO_3H$ (equivalents) | M (equivalents) | Solvent | Product (% yield) |
|---|---|---|---|---|---|
| 1 | 2,3-dimethyl-2-butene (0.054) | 1.9 | W (1.3) | 0.47 mL $C_6D_6$ | 2,3-dimethylbutane (91) |
| 2 | 2-ethyl-1-butene (0.041) | 1.7 | Mo (1.3) | 0.62 mL $CD_2Cl_2$ | 3-methylpentane (99) |
| 3 | E-3-methyl-2-pentene (0.050) | 1.1 | Mo (1.2) | 0.38 mL $CD_2Cl_2$ | 3-methylpentane (100) |
| 4 | Z-3-methyl-2-pentene (0.041) | 1.2 | W (1.3) | 0.36 mL $CD_2Cl_2$ | 3-methylpentane (100) |
| 5 | 2-methyl-1-pentene (0.049) | 1.2 | Mo (1.2) | 0.37 mL $CD_2Cl_2$ | 2-methylpentane (96) |
| 6 | 3,3-dimethyl-1-butene (0.054) | 1.1 | Mo (1.2) | 0.41 mL $CD_2Cl_2$ | 2,3-dimethylbutane (100) |
| 7 | α-methylstyrene (0.046) | 1.2 | W (1.2) | 0.41 mL $CD_2Cl_2$ | isopropylbenzene (53) |
| 8 | E-2-phenyl-2-pentene (0.041) | 1.2 | Mo (1.4) | 0.42 mL $CD_2Cl_2$ | 2-phenylpentane (97) |

In these examples, alkenes were hydrogenated at low temperatures of −75° C. The alkene, the metal hydride, and 3–4 microliters of 1,2-dichlorethane as an internal standard for $^1H$ NMR were added to a 5 mm NMR tube. Dichloromethane-$d_2$ solvent was added to give a final volume of 0.45 mL. The solution was cooled to low temperature in a constant temperature bath, then $CF_3SO_3H$ added at low temperature and the tube shaken. After 5 minutes, pyridine (15 microliters, 0.19 mmol) was added to consume any remaining acid. The tube was warmed to room temperature and the yield of hydrogenated product determined by $^1H$ NMR. Details of the examples and results are listed in Table II.

EXAMPLE 15

In this example, trans-3-methyl-2-pentene (5 microliters) and $(C_5H_5)(CO)_3WH$ (17 mg, 1.2 equivalents based on starting alkene) along with 1,2-dichloroethane (5 microliters) as an internal standard for $^1H$ NMR were added to a 5 mm NMR tube in an inert atmosphere. Dichloromethane-$d_2$ solvent was added to give a total volume of 0.45 mL. The tube was cooled to $-78°$ C. Then $CF_3SO_3H$ (9 microliters, 2.5 equivalents based on starting alkene) was added, the tube was shaken and quickly inserted into the NMR probe at $-80°$ C. After 10 minutes at $-80°$ C., an NMR spectrum indicated a 100% yield of 3-methylpentane.

EXAMPLE 16

In this example, 2,3-dimethyl-1-butene (4 microliters) and $(C_5H_5)(CO)_3WH$ (15 mg, 1.4 equivalents) along with 1,2-dichloroethane (4 microliters, internal standard) were add to a 5 mm NMR tube in an inert atmosphere.

EXAMPLE 21

Acetophenone (3 microliters, 0.026 mmoles) and $(C_5H_5)(CO)_3MoH$ (19 mg, 3.0 equivalents) in benzene-$d_6$ solvent (total volume 0.47 mL were prepared in a 5 mm NMR tube in an inert atmosphere at room temperature (about 22° C.). $CF_3SO_3H$ (1.1 equivalent) was added. A color change indicated that a reaction occurred within seconds and an $^1H$ NMR spectrum indicated the formation of ethylbenzene (32%), $\alpha$-methylbenzyl alcohol $(C_6H_5)CH(CH_3)OH$ (6%) and unreacted acetophenone (57% of initial starting material remaining). After the addition of additional $CF_3SO_3H$ (4 microliters, 0.045 mmoles), the yield of ethylbenzene was 88%.

EXAMPLE 22

Acetophonone (3 microliters, 0.026mmol) was hydrogenated as

Acetophonone (3 microliters, 0.026 mmol) was hydrogenated as in Example 21 excep that $(C_5$

TABLE II

Alkene Hydrogenations using $CF_3SO_3H$ and $(C_5H_5)(CO)_3MH$ carried out at $-75°$ C. for 5 minutes, followed by quenching the reaction with pyridine (15 microliters)

| Example | Alkene (Millimoles) | $CF_3SO_3H$ (equivalents) | M (equivalents) | Solvent $CD_2Cl_2$ (mL) | Product (% yield) |
|---|---|---|---|---|---|
| 9 | 2,3-dimethyl-2-butene (0.038) | 1.3 | W (1.5) | 0.34 | 2,3-dimethylbutane (85) |
| 10 | 2,3-dimethyl-2-butene (0.038) | 1.3 | Mo (1.5) | 0.36 | 2,3-dimethylbutane (85) |
| 11 | Z-3-methyl-2-pentene (0.033) | 2.0 | Mo (1.5) | 0.45 | 3-methylpentane (91) |
| 12 | 2-methyl-2-pentene (0.041) | 1.4 | Mo (1.6) | 0.44 | 2-methylpentane (96) |
| 13 | 2,3-dimethyl-1-butene (0.040) | 1.4 | Mo (1.5) | 0.41 | 2,3-dimethylbutane (86) |
| 14 | 2-ethyl-1-butene (0.033) | 1.4 | Mo (1.6) | 0.41 | 3-methylpentane (75) |

Dichloromethane-$d_2$ solvent was added to give a total volume of 0.63 mL. The tube was cooled to $-78°$ C. Then $CF_3SO_3H$ (8 microliters) was added, the tube was shaken and inserted into the NMR probe at $-80°$ C. After 8 minutes, an NMR spectrum indicated a 95% yield of 2,3-dimethylbutane.

EXAMPLES 17-20

In these examples, alkenes were hydrogenated using the
Examples 9-14 except triethylsilane ($HSiEt_3$) was used. Hydrogenations were carried out at $-75°$ C. for 5 minutes followed by quenching the reaction with excess pyridine (15 microliters). An exception was the hydrogenation of $\alpha$-methylstyrene which was carried out at room temperature for 5 minutes. Details and results are listed in Table III.

$H_5O(CO)_3WH$ 20 mg.

TABLE III

Alkene Hydrogenations using $CF_3SO_3H$ and $HSiEt_3$

| Example | Alkene (Millimoles) | $CF_3SO_3H$ (equivalents) | Equivalents of $HSiEt_3$ | Amount of $CD_2Cl_2$ (mL) | Product (% yield) |
|---|---|---|---|---|---|
| 17 | $\alpha$-methylstyrene (0.054) | 1.5 | 1.5 | 0.41 | isopropylbenzene (64) |
| 18 | 2-methyl-2-pentene (0.041) | 1.4 | 1.4 | 0.45 | 2-methylpentane (98) |
| 19 | 2-methyl-1-pentene (0.041) | 1.4 | 1.4 | 0.42 | 3-methylpentane (93) |
| 20 | 2,3-dimethyl-1-butene (0.040) | 1.4 | 1.4 | 0.44 | 2,3-dimethylbutane (96) |

0.060 mmol) was used. The total volume in dichloromethane-$d_2$ solvent was 0.48 mL and $CF_3SO_3H$ (5 microliters, 2.2 equivalent based on acetophenone) was added. NMR showed a 52% yield of ethylbenzene and 36% remaining acetophenone after 3 hours at room temperature. After 53 hours at room temperature, the yield of ethylbenzene was 76%.

EXAMPLE 23

The secondary benzylic alcohol, $\alpha$-methylbenzyl alcohol (3 microliters, 0.025 mmole) and $(C_5H_5)(CO)_3WH$ (14 mg, 0.043 mmoles) were prepared using the method of Example 21. Dichloromethane-$d_2$ was added to a total volume of 0.37 mL, followed by the addition of $CF_3SO_3H$ (3 microliters, 0.034 mmole) resulting in a 74% yield of ethylbenzene after 5 minutes at room temperature and a 94% yield of ethylbenzene after 30 minutes at room temperature.

EXAMPLE 24

The method of Example 23 was repeated except that molybdenum hydride $(C_5H_5)(CO)_3MoH$ was used. Similar yields were obtained.

EXAMPLE 25

A solution of tertiary alcohol, 3-methyl-3-pentanol (6 microliters, 0.049 mmol) and $(C_5H_5)(CO)_3MoH$ were prepared using the method of Example 21. Dichloromethane-$d_2$ was added to a total volume of 0.48 mL, followed by the addition of $CF_3SO_3H$ (5.5 microliters, 0.062 mmol) resulting in a 70% yield of 3-methylpentane after 20 minutes at room temperature. After 5 hours at room temperature, the yield of 3-methylpentane was about 82%.

EXAMPLE 26

The tertiary alcohol, 2-methyl-2-pentanol was hydrogenated using the method of Example 25. The product was 2-methylpentane in results comparable to those of Example 25.

EXAMPLE 27

A solution of 2-cyclopropyl-propene (4 microliters, 0.034 mmol) and $(C_5H_5)(CO)_3MoH$ (21 mg, 0.086 mmol) in dichloromethane (volume=0.48 mL) was treated with $CF_3SO_3H$ (8.5 microliters, 0.096 mmol) at room temperature. After about 10 minutes, the yield of 2-methylpentane was determined to be about 84% by $^1H$ NMR.

EXAMPLE 28

A solution of α-cyclopropylstyrene (5 microliters, 0.033 mmol) and $(C_5H_5)(CO)_3MoH$ (24 mg, 0.097 mmole) in dichloromethane-$d_2$ was treated at room temperature with $CF_3SO_3H$ (3 microliters, 0.034 mmol). A color change indicated an immediate reaction and an $^1H$ NMR after 5 minutes showed that α-cyclopropyl-ethylbenzene (58% yield) was the major product. This indicates that hydrogenation of the carbon-carbon double bond is favored over cleavage of the cyclopropyl group. Additional $CF_3SO_3H$ (5 microliters, 0.056 mmol) was added. NMR after one hour showed the major product to be 2-phenylpentane (Ca 57%). Two other products, 3-phenylpentane and β-methyl-butylbenzene, were observed in approximate yields of 14% and 7% respectively. These two products are formed due to rearrangement of the intermediate carbocation which is formed from the reaction of $CF_3SO_3H$ with α-cyclopropyl-ethylbenzene.

Examples 1-8 show that alkenes can be very rapidly hydrogenated at room temperatures with a very high yield of alkane product by adding strong acid to a solution of the alkene and a transition metal hydride. Examples 9-16 show advantageous results at exceptionally low temperatures.

Examples 17-20 demonstrate that the novel hydrogenations of the invention can be carried out using silanes.

Examples 21-22 show that aromatic ketones can be rapidly hydrogenated using transition metal hydrides. Examples 23-26 demonstrate the rapid hydrogenation of secondary benzylic alcohols and tertiary alcohols, using the invention. Example 27 shows that ring-opening can be performed. Example 28 shows that both hydrogenation of internal double bonds and ring-opening can be carried out in the same process.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

I claim:

1. A process for the non-catalytic hydrogenation of an organic compound which contains at least one reducible functional group selected from the group consisting of C=C, C—OH, C—O—C, and a strained cyclic structure, the process comprising reacting the organic compound, a hydride complex and a strong acid in a liquid phase.

2. The process of claim 1 wherein the organic compound is selected from the group consisting of alkenes, tertiary alcohols, secondary benzyl alcohols and compounds containing strained cyclic groups.

3. The process of claim 1 wherein the hydride complex is selected from the group consisting of transition metal hydridocarbonyl, hydridocyclopentadienyl and hydridocarbonylcyclopentadienyl, and organosilanes.

4. The process of claim 3 wherein the transition metal is selected from the group consisting of molybdenum, tungsten, manganese, rhenium, iron and cobalt.

5. The process of claim 1 wherein the hydride complex is selected from the group consisting of $HMo(CO)_3(C_5H_5)$, $HW(CO)_3(C_5H_5)$, $HMn(CO)_5$, $HFe(CO)_2(C_5H_5)$, $HMn(PF_3)_5$, $HRe(CO)_5$, $HCo(CO)_4$, $HCo(PF_3)_4$ and $HSi(CH_2CH_3)_3$.

6. The process of claim 1 wherein the acid has a $pK_a$ less than about 1.

7. The process of claim 1 wherein the acid is selected from the group consisting of trifluorosmethanesulfonic acid, fluorosulfonic acid, toluene sulfonic acid, tetrafluoroboric acid ether complexes, hexafluorophosphoric acid—ether complexes and sulfuric acid.

8. The process of claim 1 wherein the liquid phase is provided by a solvent selected from the group consisting of methylene chloride, toluene, mesitylene, xylene and benzene.

9. The process of claim 1 wherein the acid, organic compound and hydride complex are present in a molar ratio of about 1:1:1.

10. The process of claim 1 wherein the acid and the hydride complex are each present in an amount which is in excess of the organic compound.

11. The process of claim 1 wherein the hydrogenation is carried out at a temperature of from about −110° C. to about 110° C. and at ambient pressure.

12. A process for the hydrogenation of an aromatic ketone, the process comprising reacting the aromatic ketone, a transition metal hydride complex selected from the group consisting of $HMo(CO)_3(C_5H_5)$, $HMn(CO)_5$, $HFe(CO)_2(C_5H_5)$, $HMn(PF_3)_5$, $HRe(CO)_5$, $HCo(CO)_4$ and $HCo(PF_3)_4$ and a strong acid in a liquid phase.

13. A process for the rapid hydrogenation of a substituted alkene to an alkane, the process comprising adding a strong acid to a solution of the alkene and a hydride complex.

14. The process of claim 13 wherein the hydride complex is selected from the group consisting of $HMo(CO)_3(C_5H_5)$, $HW(CO)_3(C_5H_5)$, $HMn(CO)_5$, $HSi(C_2H_5)_3$, $H_2Si(C_2H_5)_2$, $H_2Si(C_6H_5)_2$, and $HSi(C_3H_7)_3$.

15. The process of claim 13 wherein the strong acid is selected from the group consisting of trifluoromethanesulfonic acid, fluorosulfonic acid and tetrafluoroboronic acid—diethylether complex.

16. The process of claim 13 wherein the alkene and the hydride complex are dissolved in a solvent selected from the group consisting of methylene chloride, toluene, mesitylene, xylene and benzene.

17. The process of claim 13 wherein the acid and hydride complex are introduced in an amount which is in excess of the amount of alkene.

18. The process of claim 13 wherein the process is carried out for about one second to about 10 minutes at about −110° C. to about 111° C.

19. The process of claim 13 wherein the substituted alkene is selected from the group consisting of tetra-substituted, tri-substituted and 1,1-disubstituted alkenes.

* * * * *